United States Patent
Kim et al.

(10) Patent No.: US 8,304,215 B2
(45) Date of Patent: Nov. 6, 2012

(54) GLUCONACETOBACTER STRAIN HAVING CELLULOSE PRODUCING ACTIVITY

(75) Inventors: Jong-Seong Kim, Seoul (KR); Woo-jae Lee, Yongin-si (KR); Nam-Seok Roh, Seongnam-si (KR); Sang-IL Kim, Yongin-si (KR); Min-Ho Yoon, Suwon-si (KR); Young Tak Song, Jeonju-si (KR); Tae Jin Kang, Jeonju-si (KR); Suk Heung Oh, Jeonju-si (KR); Seung-Jae Lee, Gunsan-si (KR); Hye Jin Kim, Jeonju-si (KR); Jin Ju Yu, Jeonbuk (KR); Dong Hyun Yu, Gwacheon-si (KR); Young Sik Yoon, Seoul (KR); Jong Hwan Lee, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 13/038,926

(22) Filed: Mar. 2, 2011

(65) Prior Publication Data

US 2011/0218297 A1  Sep. 8, 2011

(30) Foreign Application Priority Data

Mar. 3, 2010  (KR) .................. 10-2010-0018886
Feb. 8, 2011  (KR) .................. 10-2011-0010843

(51) Int. Cl.
  *C12P 19/04*  (2006.01)
  *C12N 1/20*  (2006.01)
(52) U.S. Cl. .................................... 435/101; 435/252.1
(58) Field of Classification Search ........................ None
  See application file for complete search history.

(56) References Cited

OTHER PUBLICATIONS

Jang, O-Y et al., Growth Characteristics and Production of Cellulose of Microorganisms in Static Culture Vinegar, Kor. J. Food Sci. Technol, 2003, vol. 35 (6): 1150-1154. (English Abstract).
Lee, O-S. et al., Culture Condition for the production of bacterial cellulose with Gluconacetobacter Persimmonus KJ145, J. Korean Soc. Food Sci Nutr., 2002, 31 (4): 572-577, (English Abstract).
Jeong, Y.J. et al., A view of utilizing cellulose produced by acetobacter bacteria, Food Industry and Nutrition, 2000, vol. 5(1) : 25-20. (English Abstract).
Krieg, N.R. et al., Bergey's Manual of Systematic Bacteriology, vol. 1, Family VI. Acetobacteraceae, 1984, Williams & Wilkins Co., USA., pp. 267-277.
Nogi, M. et al., Transparent Nanocorriposites Based on Cellulose Produced by Bacteria Offer Potential Innovation in the Electronics Device Industry, Adv. Mater. 2008, 20:1849-1852.
Park, M-H. et al., Isolation and characteristics of Acetic Acid Bacteria for Persimmon Vinegar, J. Korean Soc. Food Sci Nutr., 2005, 34 (8): 1251-1257 (English Abstract).
Schramm, M. et al., Factors affecting Production of Cellulose at the Air/Liquid Interface of a Culture of *Acetobacter xylinum*, J. gen. Microbiol., 1954, 11:123-129.
Son, H-J. et al., Isolation and Identification of cellulose-producing bacteria, Kor. J. Appl Microbiol. Biotechnol., 2000, 28 (3): 134-138. (English Abstract).

*Primary Examiner* — Tekchand Saidha
*Assistant Examiner* — Md. Younus Meah
(74) *Attorney, Agent, or Firm* — Cantor Colburn LLP

(57) ABSTRACT

Disclosed herein is a novel *gluconacetobacter* strain having cellulose producing activity. Specifically, the present invention relates to a novel *gluconacetobacter* strain producing nano-structured cellulose in a highly efficient manner. The cellulose produced by the strain, due to its superb thermodynamic properties, can be characterized as nano-structured bacterial cellulose and therefore utilized as a bio-nano-fiber. Particularly, the cellulose can be impregnated with a resin to form a cellulose-based resin which can be effectively adapted for a substrate for a liquid crystal display (LCD).

9 Claims, 12 Drawing Sheets

SEQUENCE LISTING

```
<160> NUMBER OF SEQ ID NOS: 6

<210> SEQ ID NO 1
<211> LENGTH: 1328
<212> TYPE: DNA
<213> ORGANISM: Artificial Sequence
<220> FEATURE:
<223> OTHER INFORMATION: synthetic construct: 16s rDNA of
      gluconacetobacter sp. D44
<220> FEATURE:
<221> NAME/KEY: misc_feature
<222> LOCATION: (379)..(379)
<223> OTHER INFORMATION: 'n' is a, g, c, or t.
<220> FEATURE:
<221> NAME/KEY: misc_feature
<222> LOCATION: (460)..(460)
<223> OTHER INFORMATION: 'n' is a, g, c, or t.

<400> SEQUENCE: 1
gggggcaagc gttgctcgga atgactgggc gtaaagggcg cgtaggcggt tgacacagtc      60
agatgtgaaa ttcctgggct taacctgggg gctgcatttg atacgtggcg actagagtgt    120
gagagagggt tgtgaattc ccagtgtaga ggtgaaattc gtagatattg ggaagaacac     180
cggtggcgaa ggcggcaacc tggctcatga ctgacgctga ggcgcgaaag cgtggggagc    240
aaacaggatt agataccctg gtagtccacg ctgtaaacga tgtgtgcttg gatgttgggt    300
gactttgtca ttcagtgtcg tagttaacgc gataagcaca ccgcctgggg gagtacggcc    360
nccaaggttg aaactcaang ctttcagcgg ggacgatgat gacggtaccc gcagaagaag    420
ccccggctaa cttcgtgcca gcagccgcgg taatacgaan ggggggcaagc gttgctcgga    480
```

```
atgactgggc gtaaagggcg cgtaggcggt tgacacagtc agatgtgaaa ttcctgggct      540
taacctgggg gctgcatttg atacgtggcg actagagtgt gagagagggt tgtgaaattc      600
ccagtgtaga ggtgaaattc gtagatattg gaagaacac cggtggcgaa ggcggcaacc      660
tggctcatga ctgacgctga ggcgcgaaag cgtggggagc aaacaggatt agataccctg      720
gtagtccacg ctgtaaacga tgtgtgctgg atgttgggtg actttgtcat tcagtgtcgt      780
agttaacgcg ataagcacac cgcctgggga gtacggccgc aaggttgaaa ctcaaaggaa      840
ttgacggggg cccgcacaag cggtggagca tgtggtttaa ttcgaagcaa ccgcagaacc      900
ttaccagggc ttgacatgcg gaggccgtgt ccagagatgg gcatttctcg caagagacct      960
ccagcacagg tgctgcatgg ctgtcgtcag ctcgtgtcgt gagatgttgg gttaagtccc     1020
gcaacgagcg caaccctcgc ctttagttgc cagcacgtct gggtgggcac tctaaaggaa     1080
ctgccggtga caagccggag gaaggtgggg atgacgtcaa gtcctcatgg cccttatgtc     1140
ctgggctaca cacgtgctac aatggcggtg acagtgggaa gccaggtagc gataccgagc     1200
cgatctcaaa aagccgtctc agttcggatt gcactctgca actcgagtgc atgaaggtgg     1260
aatcgctagt aatcgcggat cagcatgccg cggtgaatac gttcccgggc cttgtacaca     1320
ccgcccgt                                                              1328

<210> SEQ ID NO 2
<211> LENGTH: 1347
<212> TYPE: DNA
<213> ORGANISM: Artificial Sequence
<220> FEATURE:
<223> OTHER INFORMATION: synthetic construct: 16s rDNA of
      gluconacetobacter intermedius D47
<220> FEATURE:
<221> NAME/KEY: misc_feature
<222> LOCATION: (446)..(446)
<223> OTHER INFORMATION: 'n' is a, g, c, or t.
<220> FEATURE:
<221> NAME/KEY: misc_feature
<222> LOCATION: (448)..(448)
<223> OTHER INFORMATION: 'n' is a, g, c, or t.
<220> FEATURE:
<221> NAME/KEY: misc_feature
<222> LOCATION: (450)..(450)
<223> OTHER INFORMATION: 'n' is a, g, c, or t.
<220> FEATURE:
<221> NAME/KEY: misc_feature
<222> LOCATION: (453)..(453)
<223> OTHER INFORMATION: 'n' is a, g, c, or t.
<220> FEATURE:
<221> NAME/KEY: misc_feature
<222> LOCATION: (475)..(475)
<223> OTHER INFORMATION: 'n' is a, g, c, or t.
<220> FEATURE:
<221> NAME/KEY: misc_feature
<222> LOCATION: (483)..(483)
<223> OTHER INFORMATION: 'n' is a, g, c, or t.

<400> SEQUENCE: 2
agagtttgat catggctcag agcgaacgct ggcggcatgc ttaacacatg caagtcgcac       60
gaacctttcg ggttagtgg cggacgggtg agtaacgcgt agggatctgt ccacgggtgg      120
gggataactt tgggaaactg aagctaatac cgcatgacac ctgagggtca aaggcgcaag      180
tcgcctgtgg aggaacctgc gttcgattag ctagttggtg gggtaaaggc ctaccaaggc      240
gatgatcgat agctggtctg agaggatgat cagccacact gggactgaga cacggcccag      300
actcctacgg gaggcagcag tggggaatat tggacaatgg gcgcaagcct gatccagcaa      360
tgccgcgtgt gtgaagaagg ttttcggatt gtaaagcact tcagcgggg acgatgatga      420 cgcgtacccg cagaagaagc cccggntnan ttngtgccag cagccgcggt aatangaagg      480
```

```
ggncaagcgt tgctcggaat gactgggcgt aaagggcgcg taggcggttg acacagtcag      540
atgtgaaatt cctgggctta acctgggggc tgcatttgat acgtggcgac tagagtgtga      600
gagagggttg tggaattccc agtgtagagg tgaaattcgt agatattggg aagaacaccg      660
gtggcgaagg cggcaacctg gctcatgact gacgctgagg cgcgaaagcg tggggagcaa      720
acaggattag ataccctggt agtccacgct gtaaacgatg tgtgctggat gttgggtgac      780
tttgtcattc agtgtcgtag ttaacgcgat aagcacaccg cctggggagt acggccgcaa      840
ggttgaaact caaaggaatt gacggggccc gcacaagcg gtggagcatg tggtttaatt       900
cgaagcaacg cgcagaacct taccagggct tgacatgcgg aggccgtgtc cagagatggg      960
catttctcgc aagagacctc cagcacaggt gctgcatggc tgtcgtcagc tcgtgtcgtg     1020
agatgttggg ttaagtcccg caacgagcgc aaccctcgcc tttagttgcc atcacgtctg     1080
ggtgggcact ctaaaggaac tgccggtgac aagccggagg aaggtgggga tgacgtcaag     1140
tcctcatggc ccttatgtcc tgggctacac acgtgctaca atggcggtga cagtgggaag     1200
ccaggtggtg acaccgagcc gatctcaaaa agccgtctca gttcggattg cactctgcaa     1260
ctcgagtgca tgaaggtgga atcgctagta atcgcggatc agcatgccgc ggtgaatacg     1320
ttcccgggcc ttgtacacac cgcccgt                                          1347

<210> SEQ ID NO 3
<211> LENGTH: 20
<212> TYPE: DNA
<213> ORGANISM: Artificial Sequence
<220> FEATURE:
<223> OTHER INFORMATION: synthetic construct: forward primer for cloning
      16s rDNA

<400> SEQUENCE: 3
agagtttgat cmtggctcag                                                   20

<210> SEQ ID NO 4
<211> LENGTH: 16
<212> TYPE: DNA
<213> ORGANISM: Artificial Sequence
<220> FEATURE:
<223> OTHER INFORMATION: synthetic construct: reverse primer for cloning
      16s rDNA

<400> SEQUENCE: 4
acgggcgggt gtgtrc                                                       16

<210> SEQ ID NO 5
<211> LENGTH: 1336
<212> TYPE: DNA
<213> ORGANISM: Artificial Sequence
<220> FEATURE:
<223> OTHER INFORMATION: synthetic construct: 16s rDNA of
      Gluconacetobacter rhaeticus (AY180961)

<400> SEQUENCE: 5
tgggtggggg ataactttgg gaaactgaag ctaataccgc atgacacctg agggtcaaag       60
gcgcaagtcg cctgtggagg aacctgcgtt cgattagcta gttggtgggg taaaggccta     120
ccaaggcgat gatcgatagc tggtctgaga ggatgatcag ccacactggg actgagacac     180
ggcccagact cctacgggag gcagcagtgg ggaatattgg acaatgggcg caagcctgat     240
ccagcaatgc cgcgtgtgtg aagaaggttt tcggattgta aagcactttc agcggggacg     300
atgatgacgt tacccgcaga agaagcccg  gctaacttcg tgccagcagc cgcggtaata     360 cgaaggggc  aagcgttgct cggaatgact gggcgtaaag ggcgcgtagg cggttgttac     420
```

| | |
|---|---|
| agtcagatgt gaaattcccg ggcttaacct gggggctgca tttgatacgt gatgactaga | 480 |
| gtgtgagaga gggttgtgga attcccagtg tagaggtgaa attcgtagat attgggaaga | 540 |
| acaccggtgg cgaaggcggc aacctggctc atgactgacg ctgaggcgcg aaagcgtggg | 600 |
| gagcaaacag gattagatac cctggtagtc cacgctgtaa acgatgtgtg ctggatgttg | 660 |
| ggtgactttg tcattcagtg tcgtagttaa cgcgataagc acaccgcctg ggagtacgg | 720 |
| ccgcaaggtt gaaactcaaa ggaattgacg ggggcccgca caagcggtgg agcatgtggt | 780 |
| ttaattcgaa gcaacgcgca gaaccttacc agggcttgac atgcggaggc tgtgtccaga | 840 |
| gatgggcatt tctcgcaaga gacctccagc acaggtgctg catggctgtc gtcagctcgt | 900 |
| gtcgtgagat gttgggttaa gtcccgcaac gagcgcaacc ctcgcctttta gttgccatca | 960 |
| cgtctgggtg gcactctaa aggaactgcc ggtgacaagc cggaggaagg tggggatgac | 1020 |
| gtcaagtcct catggccctt atgtcctggg ctacacacgt gctacaatga cggtgacagt | 1080 |
| gggaagccag gtggtgacac cgagccgatc tcaaaaagcc gtctcagttc ggattgcact | 1140 |
| ctgcaactcg agtgcatgaa ggtggaatcg ctagtaatcg cggatcagca tgccgcggtg | 1200 |
| aatacgttcc cgggccttgt acacaccgcc cgtcacacca tgggagttgg tttgaccta | 1260 |
| agccggtgag cgaaccgcaa ggacgcagcc gaccacggtc gggtcagcga ctggggtgaa | 1320 |
| gtcgtaacaa ggtagc | 1336 |

<210> SEQ ID NO 6
<211> LENGTH: 1345
<212> TYPE: DNA
<213> ORGANISM: Artificial Sequence
<220> FEATURE:
<223> OTHER INFORMATION: synthetic construct: 16s rDNA of
      Gluconacetobacter intermedius (Y14694)

<400> SEQUENCE: 6

| | |
|---|---|
| gagtttgatc mtggctcaga gcgaacgctg gcggcatgct taacacatgc aagtcgcacg | 60 |
| aacctttcgg ggttagtggc ggacgggtga gtaacgcgta gggatctatc cacgggtggg | 120 |
| ggataacttt gggaaactga agctaatacc gcatgacacc tgagggtcaa aggcgcaagt | 180 |
| cgcctgtgga ggaacctgcg ttcgattagc tagttggtgg ggtaaaggcc taccaaggcg | 240 |
| atgatcgata gctggtctga gaggatgatc agccacactg gactgagac acggcccaga | 300 |
| ctcctacggg aggcagcagt ggggaatatt ggacaatggg cgcaagcctg atccagcaat | 360 |
| gccgcgtgtg tgaagaaggt tttcggattg taaagcactt tcagcgggga cgatgatgac | 420 |
| ggtacccgca gaagaagccc cggctaactt cgtgccagca gccgcggtaa tacgaagggg | 480 |
| gcaagcgttg ctcggaatga ctgggcgtaa agggcgcgta ggcggttgac acagtcagat | 540 |
| gtgaaattcc cgggcttaac ctgggggctg catttgatac gtggcgacta gagtgtgaga | 600 |
| gagggttgtg gaattcccag tgtagaggtg aaattcgtag atattgggaa gaacaccggt | 660 |
| ggcgaaggcg gcaacctggc tcatgactga cgctgaggcg cgaaagcgtg gggagcaaac | 720 |
| aggattagat accctggtag tccacgctgt aaacgatgtg tgctggatgt tgggtgactt | 780 |
| tgtcattcag tgtcgtagtt aacgcgataa gcacaccgcc tggggagtac ggccgcaagg | 840 |
| ttgaaactca aaggaattga cggggccccg cacaagcggt ggagcatgtg gtttaattcg | 900 |
| aagcaacgcg cagaacctta ccagggcttg acatgcggag gccgtgtcca gagatgggca | 960 |
| tttctcgcaa gagacctcca gcacaggtgc tgcatggctg tcgtcagctc gtgtcgtgag | 1020 |
| atgttgggtt aagtcccgca acgagcgcaa ccctcgcctt tagttgccat cacgtttggg | 1080 |
| tgggcactct aaaggaactg ccggtgacaa gccggaggaa ggtggggatg acgtcaagtc | 1140 |

-continued

```
ctcatggccc ttatgtcctg ggctacacac gtgctacaat ggcggtgaca gtgggaagcc    1200
aggtggtgac accgagccga tctcaaaaag ccgtctcagt tcggattgca ctctgcaact    1260
cgagtgcatg aaggtggaat cgctagtaat cgcggatcag catgccgcgg tgaatacgtt    1320
cccgggcctt gtacacaccg cccgt                                         1345
```

GLUCONACETOBACTER STRAIN HAVING CELLULOSE PRODUCING ACTIVITY

CROSS REFERENCE TO RELATED APPLICATIONS

This application claims priority to Korean Patent Application No. 10-2010-0018886, filed Mar. 3, 2010, and Korean Patent Application No. 10-2011-0010843, filed Feb. 8, 2011, and all the benefits accruing therefrom under 35 U.S.C. §119, which are hereby incorporated by reference for all purposes as if fully set forth herein.

BACKGROUND OF THE INVENTION (a) Field of the Invention

The present invention relates to a novel *gluconacetobacter* strain having cellulose producing activity. Specifically, the present invention relates to a novel *gluconacetobacter* strain capable of producing nano-structured cellulose in a highly efficient manner.

(b) Description of the Related Art

Cellulose is one of the most abundant natural macromolecules on Earth with about $10^{11}$ ton estimated to be naturally synthesized, most of which is biosynthesized to be the structural component of cell wall fibers of higher plants. Its high tensile strength is mainly due to its overall structure. Cellulose molecules form a chain or microfibril whose length ranges to 14,000 units, which in turn is structured into a twisted rope-shaped bundle maintained by hydrogen bonds. On the basis of its characteristics of being abundant and having unique physical properties, many studies with regard to its possible industrial applicability as a regenerating resource have been performed.

Since A. J. Brown reported in 1886 that *Acetobacter* produced cellulose, Bacterial Cellulose (BC) produced by a microorganism has become the subject of continuous studies as a new material. In particular, it has been discovered that microorganism-derived BC forms ribbon-like bundles, whereas plant-derived cellulose forms bundles of microfibrils.

In contrast to microfibril bundles formed by plant-derived cellulose, the ribbon-like bundles formed by microorganism-derived BC are produced in their pure state in the absence of lignin or hemicelluloses. The unique advantageous characteristics of BC such as high mechanical strength, high water absorption, high crystallizability, and biodegradability promote development of its diverse applications in a variety of industrial fields.

Currently, despite its high cost, s-glass has been selected as a suitable material for substrates of liquid crystal displays (LCDs) due to its properties, including low heat expansion coefficient, high permeability, and micro-thickness. It has been reported that LCD substrate thermodynamic properties can be enhanced relative to those of s-glass by using nano-structured cellulose, which can be produced by microorganisms. (Schraamm, M. and S. Hestrin. 1054. Factors affecting production of cellulose at the air/liquid interface of a culture of *Acetobacter xylinum*. J. Gen. Microbiol. 11:123-129). Therefore, it is desirable as well as cost-effective to develop a microorganism that is more efficient in producing cellulose.

Although it is well-known that *acetobacter xylinum* can produce BC, its inefficiency in production of cellulose has called for a novel organism that can replace it.

SUMMARY OF THE INVENTION

The present invention is directed to a novel *gluconacetobacter* strain effectively producing cellulose.

Therefore, disclosed herein is a gluconacetobacter sp. D44 strain having Accession No: KCCM11078P or *gluconacetobacter intermedius* D47 strain having Accession No: KCCM11079P which shows cellulose producing activity.

In an embodiment, a culture of the *gluconacetobacter* strain is also disclosed.

In an embodiment, a composition comprising at least one selected from the group consisting of the *gluconacetobacter* strain, a culture thereof, and a concentrate or a dried product of the strain or the culture is disclosed.

In an embodiment, a method of producing cellulose comprising the steps of: culturing the *gluconacetobacter* strain according to claim 1; and obtaining cellulose from the culture is disclosed.

In an embodiment, a method of producing a cellulose-based resin comprising the steps of: preparing the cellulose produced by the *gluconacetobacter* strain according to claim 1; and impregnating the cellulose with a resin is disclosed.

At least one of the above and other features and advantages of the present invention may be realized by providing a *gluconacetobacter* strain having Accession No: KCCM11078P or *gluconacetobacter intermedius* strain having Accession No: KCCM11079P which shows cellulose producing activity.

At least one of the above and other features and advantages of the present invention may be realized by the culture of *gluconacetobacter* strain.

At least one of the above and other features and advantages of the present invention may be realized by providing a composition comprising at least one selected from the group consisting of the *gluconacetobacter* strain, the culture thereof, and a concentrate or a dried product of the strain or the culture.

At least one of the above and other features and advantages of the present invention may be realized by providing a method of producing cellulose comprising the steps of: culturing the *gluconacetobacter* strain according to claim 1; and obtaining cellulose from the culture.

At least one of the above and other features and advantages of the present invention may be realized by providing a method of producing a cellulose-based resin comprising the steps of: preparing the cellulose produced by the *gluconacetobacter* strain according to claim 1; and impregnating the cellulose with a resin (Masaya Nogi and Hiroyuki Yano, Transparent Nanocomposites Based on Cellulose Produced by Bacteria Offer Potential Innovation in the Electronics Device Industry, Advanced materials 2008, pp 1849-1852).

BRIEF DESCRIPTION OF THE DRAWINGS

The above and other aspects, advantages and features of this disclosure will become more apparent by describing in further detail exemplary embodiments thereof with reference to the accompanying drawings, in which:

FIGS. 2A, 2B, and 2C present a sequence alignment of 16s rDNA of D44 strain (upper sequence in FIGS. 2A, 2B, and 2C is SEQ ID NO:1) with 16s rDNA of *Gluconacetobacter rhaeticus* (lower sequence in FIGS. 2A, 2B, and 2C is SEQ ID NO:5, AY180961) in which the symbol "*" below the aligned sequences represents a position having identical nucleotides in the two aligned sequences.

FIGS. 6A, 6B, and 6C present a sequence alignment of 16s rDNA of D47 strain (upper sequence in FIGS. 6A, 6B, and 6C is SEQ ID NO:2) with 16s rDNA of *Gluconacetobacter intermedius* (lower sequence in FIGS. 6A, 6B, and 6C is SEQ ID NO:6, Y14694) in which the symbol "*" below the aligned sequences represents a position having identical nucleotides in the two aligned sequences.

DETAILED DESCRIPTION OF THE EMBODIMENTS

Figure 1:
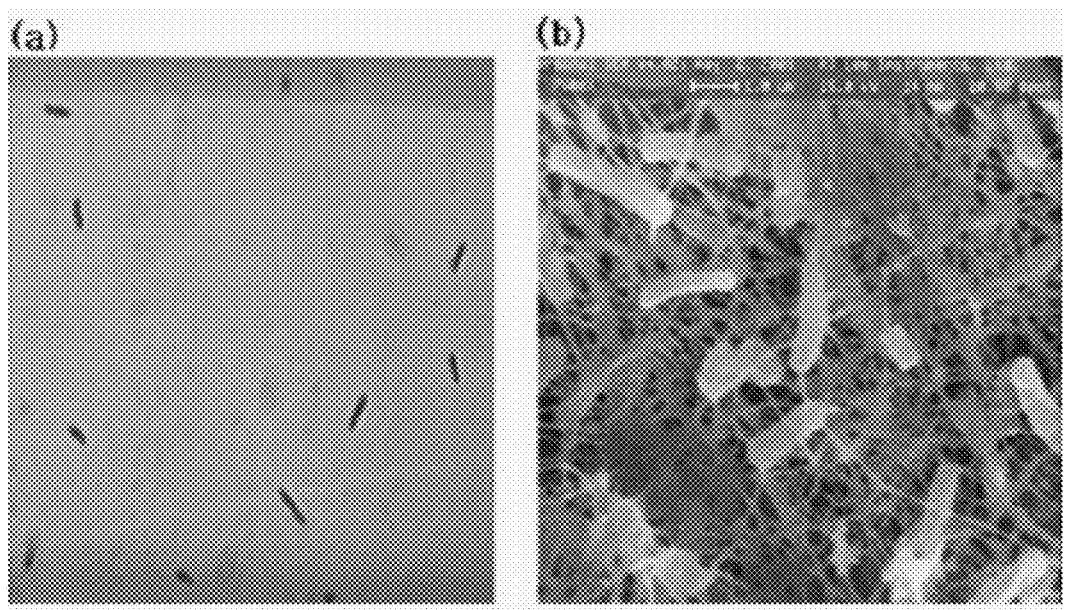
FIGS. 1 (*a*) and (*b*) show images observed by optical microscopy and scanning electron microscopy (SEM), respectively, of the morphological structure of the D44 strain disclosed herein.

The present invention is further explained in more detail below.

The present invention relates to novel *gluconacetobacter* strains having excellent cellulose producing activity. Specifically, the present invention provides a *gluconacetobacter* strain with excellent cellulose producing activity having *gluconacetobacter* sp. D44 strain having Accession No: KCCM11078P or *gluconacetobacter intermedius* D47 strain having Accession No: KCCM11079P.

A strain of the present invention is a species belonging to the acetobacteraceae family. Though not limited thereto, the strain of the present invention could be isolated from a vinegar class. Preferably, the strain could be isolated from persimmon vinegar, and more preferable, from the surface of persimmon vinegar.

According to one embodiment of the present invention, the strain having cellulose producing activity is isolated from the surface of persimmon vinegar, and the cellulose producing activity can be determined by any method known to those skilled in the art. For example, this includes, but is not limited to, inoculating H.S. culture medium (Table 1) with the strain disclosed herein to determine formation of cellulose at the air-liquid interface of the culture or inoculating Carr culture medium (Table 1) with the strain disclosed herein to determine a color transformation (Example 1).

The analysis of both morphological and biochemical characteristics of the strain of the present invention, shown in Table 2, and Table 3 (D44) and Table 4 (D47), respectively (Example 2), indicates that the strain is a *gluconacetobacter* strain.

In addition, the strains of the present invention was analyzed to determine whether it is a novel *gluconacetobacter* strain by obtaining its 16s rDNA sequence, shown in SEQ ID No: 1 and SEQ ID No: 2, respectively, and comparing the sequences to the 16s rDNA sequences of other known gluconacetobacter strains. The results showed that the 16s rDNA of the D44 strain disclosed herein showed the most homology to the 16s rDNA of *Gluconacetobacter rhaeticus*, however the percent homology was only 87.215%, and the 16s rDNA of the D47 strain disclosed herein showed the most homology to the 16s rDNA of *Gluconacetobacter intermedicus*, the percent homology was 99.776%. This indicates that the strains of the present invention is novel gluconacetobacter strains (Example 2).

The isolated and identified *gluconacetobacter* strains disclosed herein were deposited with the Korean Culture Center of Microorganisms (KCCM) on Mar. 26, 2010, and designated as Accession No: KCCM11078P and Accession No: KCCM11079P, respectively.

A culture of the *gluconacetobacter* strain of the present invention can be prepared using a culture medium and culture methods known in the art for their use in culturing microorganisms.

In culturing the *gluconacetobacter* strain of the present invention, culture media for microorganisms, specifically culture media for acetobacteraceae, and more specifically the culture media disclosed in Table 1 or Table 7 can be selected according to the desired objectives to be achieved. Most specifically, to produce cellulose, a culture medium for cellulose production, particularly, H.S. culture medium listed in Table 1 or coconut mixed medium (2) listed in Table 7, can be used (Example 4).

D44 strain can be preferably cultured either in H.S. medium comprising glucose 20 g/L, yeast extract 5 g/L, peptone 5 g/L, $Na_2HPO_4$ 2.7 g/L and sodium citrate 1.15 g/L or in coconut liquid medium consisting of undiluted coconut solution 100% (w/v). The yeast from the yeast extract (CAS No: 8013-01-02) (EINECS No: 232-387-9) contains no more than 40% of proteins, and can be gold and silver colored flake or powder with a physiochemical property of unique odor and no fermentability containing no more than 0.12 mg of thiamine hydrochloride per gram, no more than 0.04 mg of riboflavin and no more than 0.25 mg of nicotinic acid.

D47 strain can be preferably cultured in a medium comprising H.S. medium, coconut liquid medium or undiluted coconut solution, sugar, and ammonium sulphate. More preferably, the strain can be cultured in coconut mixed medium comprising undiluted coconut solution 85~94.9 part by weight, sugar 5~15 part by weight, and ammonium sulphate 0.1~1 part by weight.

Ammonium sulphate refers to white crystal structured obtained by reacting sulfuric acid and ammonia, and ammonium sulphate with a purity of preferably, 10-99.9%, more preferably, 10-30% and most preferably 15-25% can be used.

A culture of the present invention can be prepared by inoculating the culture medium with the strain disclosed herein, or by any microorganism culturing method known to those skilled in the art, such as for example, but not limited to, stationary culture or spinner culture. Specifically, an acetobacteraceae culturing method can be used and, more specifically, the culture medium can be inoculated with the strain of the present invention at 1 weight % (based on the total weight of culture medium) and cultured for 4-7 days at 28~30° C., most preferably at 30° C., to produce the culture.

Preferably, a culture of the present invention may contain cellulose produced by the strain of the present invention, but is not limited thereto.

A composition of the present invention for cellulose production comprises at least one selected from the group consisting of the *gluconacetobacter* strain disclosed herein, a culture thereof, and a concentrate or a dried product of the strain or the culture.

Since the strain of the present invention can produce cellulose in an efficient manner, the strain, a culture of the strain, a concentrate or a dried product of the strain or the culture are well suited for use as a composition for cellulose production.

A method of preparing a culture of the strain is described as the above. Specifically, this includes, but is not limited to, inoculation of a culture medium for cellulose production, or H.S. culture medium disclosed in Table 1, or coconut mixed medium (2) disclosed in Table 7, with the strain of the present invention. The culture can be produced specifically by for example, but is not limited to, a stationary culture or a spinner culture, and more specifically by stationery culture. A concentrate or a dried product of the strain or the culture thereof can be prepared according to any suitable method known to those skilled in the art for concentrating or drying microorganisms or a culture of microorganisms.

A composition for producing cellulose may contain at least one selected from the group consisting of the *gluconacetobacter* strain, a culture thereof, and a concentrate or a dried product of the strain or the culture, but is not limited thereto. Specifically, the composition may comprise at least one selected from the group consisting of the *gluconacetobacter* strain, a culture thereof, a concentrate or a dried product of the strain or the culture, for example, at 1 wt % of the composition.

A method for producing cellulose of the present invention includes culturing the *gluconacetobacter* strain disclosed herein, and obtaining cellulose from the culture. In some embodiments, culturing the *gluconacetobacter* strain D44 or D47 is performed under conditions such that cellulose is produced.

Culturing the strain may be carried out according to the method described above. In the method for producing cellulose, the cellulose formed during culturing of the strain of the present invention can be, for example, immersed in sodium hydroxide and purified by washing with distilled water, but is not limited thereto. The resultant cellulose can be, for example, in the form of a film (Example 3).

The cellulose produced by the strain of the present invention is characterized as having a smooth, firm and elastic surface, and a thickness of approximately 0.3-12 mm which is noticeably improved thickness compared to existing bacterial cellulose (Example 3 and Example 4). It is also classified as a nano-structured cellulose having a feature of a superb thermodynamic property.

Moreover, the strain of the present invention has excellent cellulose production activity. In particular, the strain can produce cellulose at a rate 3-97.5 times as efficient as *acetobacter xylinum*, a microorganism widely known for producing bacterial cellulose (Example 3 and Example 4).

The cellulose produced by the strain of the present invention, due to its superb thermodynamic property, can be characterized as nano-structured bacterial cellulose and therefore utilized as a bio-nano-fiber.

A method for producing a cellulose-based resin can include the steps of preparing cellulose produced by the *gluconacetobacter* strain; and impregnating the cellulose with a resin.

Impregnating the cellulose with a resin to produce the cellulose-based resin can be performed by a method known to those of skill in the art (Masaya Nogi and Hiroyuki Yano, Transparent Nanocomposites Based on Cellulose Produced by Bacteria Offer Potential Innovation in the Electronics Device Industry, Advanced materials 2008, pp 1849-1852). This includes, for example, but is not limited to, mixing the cellulose produced by the gluconacetobacter strain of the present invention with a thermoplastic resin and a bonding agent, and thereafter extruding the resultant mixture.

The thermoplastic resin can preferably be selected from the group consisting of polypropylene, polyethylene, polystyrene, and polyvinylchloride. The bonding agent can preferably comprise at least one selected from the group consisting of maleate ethylene, maleate propylene, and silane. At least one additive selected from the group consisting of stabilizer, pigment, dye, inorganic/organic additives, and electromagnetic shielder or a mixture thereof, can be additionally included in the mixture containing the cellulose, thermoplastic resin, and bonding agent.

The cellulose-based resin prepared according to the method described above contains nano-structured bacterial cellulose having an excellent thermodynamic property, which allows the resin to be adapted for the use as a substrate material for liquid crystal display (LCD).

Accordingly, the present invent ion relates to a method of producing a cellulose-based resin and provides a method of producing LCD substrate comprising the steps of producing a cellulose-based resin; and producing a LCD substrate using the cellulose-based resin.

In addition, the present invention provides a LCD substrate using the cellulose-based resin.

It has been reported that cellulose produced by bacteria protects the cells from any lethal effect caused by UV light, and allows the formation of bacterial cluster, which in turn promotes shielding effect from the competitors who share the same nutrient source as well as moisturization of the cell.

Characteristics of the bacterial cellulose, including high crystallization ability and high water absorption, allow for its application in diverse industrial areas, such as in a speaker vibration pad. Furthermore, the bacterial cellulose in its gel state feels pleasant to the skin and easily integrates with the outer skin. Bacterial cellulose made by the strain disclosed herein can be made into a medical or a cosmetic pad (for example, a facial mask sheet) or an artificial skin because of its ability of retaining ingredients and moisture on the epidermis. Moreover, it has been reported that when a cellulose membrane is treated with 5% NaOH or 0.5% NaCl to remove components other than cellulose and the product thereof is pressurized, a membrane having high elasticity is formed. Such a membrane, for example, is used as a speaker vibration pad in a high-performance headset manufactured by Sony in Japan.

The solidity and elasticity of paper containing bacterial cellulose are enhanced by 2.5 fold relative to the control group. In comparison with a synthetic fiber, a sheet with better qualities including superior solidity, heat stability, and structural stability can be achieved if 5-20% of the cellulose is added to a synthetic polymer fiber, aromatic polyamide or polyamide staple fiber. When a mixture containing cellulose and a synthetic or glass fiber is constructed as a sheet, it can also be used as an air filter, a wiring substrate for a printer, or a floor material.

The cellulose produced by the microorganism of the present invention is diversely applicable as an industrial and dietary material, especially considering the fact that it is environment-friendly (Jeong., Y. J., Lee., I. S. A view of utilizing cellulose produced by *acetobacter* bacteria. Food Industry and Nutrition, Vol. 5, pp. 25-29, 2000).

Due to its superb thermodynamic properties, the cellulose produced by the strain of the present invention, which is characterized to be nano-structured bacterial cellulose, can be utilized as a bio-nano-fiber. Particularly, the cellulose can be impregnated with a resin to produce a cellulose-based resin, which can be effectively used as a substrate material for LCD.

The present invention is further explained in more detail with reference to the following examples. These examples, however, should not be interpreted as limiting the scope of the present invention in any manner.

REFERENCE EXAMPLE 1

Culture Media Used in the Experiment and Culturing Conditions

In order to isolate and identify the novel strain disclosed herein, the culture media listed in Table 1 were used. Unless stated otherwise in the example below, the novel strain disclosed herein was cultured using the culture medium for 7 days at 30° C.

TABLE 1

Types of culture media and their compositions

| Culture medium | Composition | Related Literature |
|---|---|---|
| H.S culture medium | Glucose 20 g/L, Yeast extract 5 g/L, Peptone 5 g/L, Na2HPO4 2.7 g/L, sodium citrate 1.15 g/L, pH 5.0 | Schraamm, M. and S. Hestrin. 1054. Factors affecting production of cellulose at the air/liquid interface of a culture of *Acetobacter xylinum*. J. Gen. Microbiol. 11: 123-129. |
| GYC culture medium | Glucose 50 g/L, Yeast extract 10 g/L, Calcium Carbonate 30 g/L, and Agar 25 g/L | Jang, O. Y., Joo, K. H., Lee, J. H., Baik, C. G., Growth Characteristics and Production of Celulose of Microorganisms in Static Culture Vinegar. Korean J. Food Sci. Tech., Vol. 35, No. 6, pp. 1150~1154(2003) |
| Frateur culture medium | Ethanol 30 ml/L, Yeast Extract 10 g/L, Peptone 10 g/L Calcium Carbonate 10 g/L and Agar 20 g/L | Krig, N. R., J. G. Holt. 1984. Bergey's Manual of Systematic Bacteriology Vol. 1. The William and Wilkins Co., U.S.A., pp. 267-277. |
| Carr culture medium | Yeast Extract 30 g/L, Ethanol 20 ml/L, Bromocresol purple 0.022 g/L, Agar 20 g/L, pH 6.0 | Krig, N. R., J. G. Holt. 1984. Bergey's Manual of Systematic Bacteriology Vol. 1. The William and Wilkins Co., U.S.A., pp. 267-277. |
| YEG Solid culture medium | Yeast Extract 10 g/L, Glycerol 30 g/L, Agar 20 g/L | Jang. O. Y., Joo. K. H., Lee. J. H., Baik. C. G. 2003. Growth characteristics and production of cellulose of microorganisms in static culture vinegar. Korean J. Food Sci. Tech. vol. 35, No. 6, pp. 1150~1154. |
| SM culture medium | Yeast Extract 5 g/L, Glucose 50 g/L | Jang. O. Y., Joo. K. H., Lee. J. H., Baik. C. G. 2003. Growth characteristics and production of cellulose of microorganisms in static culture vinegar. Korean J. Food Sci. Tech. vol. 35, No. 6, pp. 1150~1154. |
| YPC culture medium | Yeast extract 5 g/L, Peptone 5 g/L, Calcium carbonate 5 g/L | Jang. O. Y., Joo. K. H., Lee. J. H., Baik. C. G. 2003. Growth characteristics and production of cellulose of microorganisms in static culture vinegar. Korean J. Food Sci. Tech. vol. 35, No. 6, pp. 1150~1154. |
| GYP culture medium | Glucose 30 g/L, Yeast Extract 5 g/L, Peptone 2 g/L | Jang. O. Y., Joo. K. H., Lee. J. H., Baik. C. G. 2003. Growth characteristics and production of cellulose of microorganisms in static culture vinegar. Korean J. Food Sci. Tech. vol. 35, No. 6, pp. 1150~1154. |

EXAMPLE 1

Isolation of Novel Strain Producing Cellulose

EXAMPLE 1-1

Isolation of *Gluconacetobacter* D44 Strain

The strain disclosed herein was isolated from the surface of traditional persimmon vinegar (Jeonbuk Wanju-gun Bong-dong-eup Yulso-ri, South Korea). Specifically, various regions of the persimmon vinegar were extracted, and designated as A, B, C, and D according to the extracted region. D was a sample obtained from the surface of the persimmon vinegar.

100 ml H.S. culture medium was inoculated with 1% of an undiluted solution of the persimmon vinegar samples A, B, C, or D and cultured for 7 days at 30° C. Upon completion of culturing, a homogeneous strain from sample D which produced cellulose at the air-liquid interface of the H.S. culture medium was diluted at a concentration of $10^{-7}$ and smeared over a solid H.S. culture medium. Liquid H.S. culture medium was inoculated with randomly selected colonies from the solid H.S. culture. Among these, the strain that formed cellulose at the air-liquid interface of the culture medium was selected and isolated.

Carr culture medium containing bromocresol purple having a discoloration range of pH 5.2-6.8 was also inoculated with the strain isolated from the D portion of the persimmon vinegar and then tested to see if there were color transformations from yellow to purple and from purple to yellow. Such color transformations demonstrate that the strain has a oxidation pathway which oxidizes ethanol to acetic acid and reoxidizes to carbon dioxide and water. These results confirm that the strain showed cellulose production activity (Jang. O. Y., Joo. K. H., Lee. J. H., Baik. C. G. 2003. Growth characteristics and production of cellulose of microorganisms in static culture vinegar. Korean J. Food SCI. tech. vol. 35, No. 6, pp. 1150-1154).

The strain that showed cellulose production activity was designated as the "D44" strain.

EXAMPLE 1-2

Isolation of *Gluconacetobacter intermedius* D47 Strain

The strain disclosed herein was isolated from the surface of traditional persimmon vinegar (Jeonbuk Wanju-gun Bong-dong-eup Yulso-ri, South Korea). Specifically, the epithelium that comes out when producing the traditional persimmon vinegar was obtained from Nong-Hyup (South Korea), and was sufficiently cut with a sterilized scissor for dissection. Then, the small amount was inoculated into H.S. medium and cultured for 7 days at 30° C. Upon completion of culturing, a homogeneous strain from sample which produced cellulose at the air-liquid interface of the H.S. culture medium was diluted at a concentration of $10^{-7}$ and smeared over a solid H.S. culture medium. Liquid H.S. culture medium was inoculated with randomly selected colonies from the solid H.S. culture. Among these, the strain that formed cellulose at the air-liquid interface of the culture medium was selected and isolated.

Carr culture medium containing bromocresol purple having a discoloration range of pH 5.2-6.8 was also inoculated with the strain isolated from the surface of the persimmon vinegar and then tested to see if there were color transformations from yellow to purple and from purple to yellow. Such color transformations demonstrate that the strain has a oxidation pathway which oxidizes ethanol to acetic acid and reoxidizes to carbon dioxide and water. These results confirm that the strain showed cellulose production activity (Jang. O. Y., Joo. K. H., Lee. J. H., Baik. C. G. 2003. Growth characteristics and production of cellulose of microorganisms in static culture vinegar. Korean J. Food SCI. tech. vol. 35, No. 6, pp. 1150-1154).

The strain that showed cellulose production activity was designated as the "D47" strain.

EXAMPLE 2

Identification and Deposit of Novel Strain Producing Cellulose

EXAMPLE 2-1

Morphological Features

The size, shape, Gram staining, colony shape, and colony color of the D44 strain and the D47 strain selected and isolated in Example 1 were studied, respectively. Specifically, the colonies of D44 strain and D47 strain were examined in GYC culture medium and the cellulose produced by the D44 and D47 were observed in the presence of the bacteria by optical microscopy and scanning electron microscopy (SEM).

More specifically, an optical microscope (Nikon ECLIPSE E600, Japan) was used to identify the each strain morphology and Gram staining. Furthermore, SEM was used to identify the size of the bacteria and the cellulose fiber produced thereby. Particularly, SEM was performed using the modified Chae's method (Chae. C. M. 1977. Maceration methods for SEM observation 'A legal medicine lecture room'. Kyungpook National University. p 40-58). The D44 and the D47 bacterial bodies were pre-fixed with 2% (v/v) Glutaraldehyde for 2 hr, post-fixed with 2% (w/v) $OsO_4$ for 2 hr, and then dehydrated with ethanol. After treating with isoamyl acetate, the resultant was dried at 55° C., followed by coating with gold. The results are shown in Table 2, FIG. 1, and FIG. 5.

TABLE 2

| Morphological features of D44 strain and D47 strain | | |
|---|---|---|
| Morphological Characteristic | D44 | D47 |
| Gram Staining | Negative | Negative |
| Cell Shape | Rod-shaped (bacillus) | Rod-shaped (bacillus) |
| Cell size(μm) | 0.5 × 1.8 μm | 0.6~0.8 × 1.6~2.0 um |
| Spore Formation | Negative | Negative |
| Colony Shape | Convex | Convex |
| Colony Color | White | Pale Yellow |
| Colony Surface | Smooth and Rough | Smooth and Rough |
| Colony Transparency | Opaque | Opaque |

Figure 5:
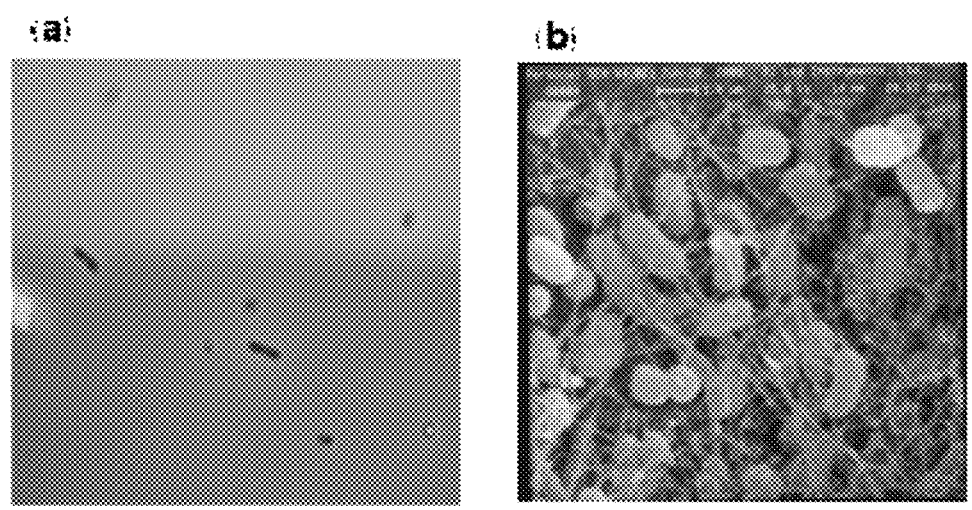
FIGS. 5 (a) and (b) show images observed by optical microscopy and scanning electron microscopy (SEM), respectively, of the morphological structure of the D47 strain disclosed herein.

As described in Table 2, FIG. 1 and FIG. 5, the D44 and the D47 strains are Gram negative, do not form a spore, and can be solitary or a pair (a diplobacilli). Specifically, as shown in FIG. 1 and FIG. 5, the strains exist inside the cellulose produced by the D44 and the D47 strain.

EXAMPLE 2-2

Biochemical Features

In order to examine the biochemical features of the D44 and the D47 strains, the strains were cultured in H.S. liquid culture medium respectively and the extracted bacterial liquid was sub-cultured in a new culture medium.

Specifically, the novel D44 and D47 strains of the present invention were cultured in Frateur culture medium and then the ethanol oxidation path was identified by determining the neutralization of $CaCO_3$ in the culture medium.

In order to examine ketogenesis in glycerol after culturing the bacteria on YEG solid culture medium for 5 days at 30° C., a few drops of Fehlings solution was applied over the colony to check whether there was an orange color transformation.

Furthermore, to examine strain growth and cellulose production in the presence of ethanol and sodium chloride, growth of the D44 strain was observed in SM culture medium with 0.5% (w/v), 1.0% (w/v), 1.5% (w/v), or 2.0% (w/v) sodium chloride added or 10% (v/v) ethanol added, followed by stationary culturing for 7 days at 30° C.

In addition, the D44 and the D47 strain were smeared over GYC solid culture medium followed by culturing for 7 days at 30° C., and subsequently brown pigment formation was examined. In order to determine the formation of γ-pyrone, the bacteria was cultured on solid YPC culture medium containing 50 g/L glucose and 50 g/L fructose for 7 days at 30° C., and then a 5% (w/v) ferric chloride solution was dropped onto the culture. Formation of γ-pyrone by the strain using the glucose and fructose is indicated by a color transformation to purple. (Jang. O. Y., Joo. K. H., Lee. J. H., Baik. C. G. 2003. Growth characteristics and production of cellulose of microorganisms in static culture vinegar. Korean J. Food Sci. Tech. vol. 35, No. 6, pp. 1150-1154).

To see the resistance of the D44 and the D47 strain against acetic acid, the D44 and the D47 strain were grown in GYP culture medium in which acetic acid concentration was adjusted to 2% (v/v)~10% (v/v), followed by culturing for 7 days at 30° C.

Additional biochemical experiments to identify the strain were performed using an API 20NE kit (Bio-Merieux, France). The strain was identified from the results using Bergy's Manual of Systematic Bacteriology (Krig, N. R., J. G. Holt. 1984. Bergey's Manual of Systematic Bacteriology Vol. 1. The William and Wilkins Co., U.S.A.).

These experimental results (summarized in Table 3 and Table 4) were compared to an *acetobacter* strain (*Acetobacter xylinum*, KCCM40274), a *gluconobacter* strain (*Gluconobacter oxidans*, KCCM21183) and a *gluconacetobacter* strain. The *gluconacetobacter* strain (*Gluconacetobacter persimmonensis*, KJ145) was disclosed in Lee. et al. (Lee. O. S., Jang. S. Y., Jeong. Y. J. 2002. Effect of Ethanol on the Production of Cellulose and Acetic Acid by *Gluconacetobacter persimmonensis* KJ145. J. Korean Soc. Food Sci. Nutr. 31 (4). 572-577.)

TABLE 3

Biochemical features of D44 strain

| Feature | D44 | *Acetobacter xylinum* KCCM40274 | *Gluconobacter oxidans* KCCM21183 | *Gluconacetobacter persimmonensis* KJ145 |
|---|---|---|---|---|
| Overoxidation of ethanol | +[1] | + | −[2] | + |
| Ketogenesis from glycerol | + | + | + | + |
| Oxidation of acetate to $CO_2$ and $H_2O$ | + | + | − | + |
| Oxidation of lactate to $CO_2$ and $H_2O$ | − | + | − | + |
| Oxidation of Fructose to $CO_2$ and $H_2O$ | + | | ND | |
| Brown pigmentation on GYC agar | − | + | − | − |
| Cellulose formation | + | + | − | + |
| Oxidase | − | − | − | − |
| Indole production | − | − | − | − |
| Urease | − | − | − | − |
| γ-pyrone from 5% glucose | − | − | + | − |
| γ-pyrone from 5% fructose | − | − | + | − |
| β-galactocidase | + | + | − | + |
| Nitrate to nitrite | + | + | + | − |
| Gelatin liquefaction | − | − | − | − |
| Acid produced from | | | | |
| Arabinose | − | − | − | + |
| Manose | − | ± | + | + |
| Manitol | + | + | + | + |
| Glucose | + | + | + | + |
| Growth in the presence of | | | | |
| 10% ethanol | − | − | − | − |
| 0.5% NaCl | + | | ND[3] | |
| 1.0% NaCl | + | | | |
| 1.5% NaCl | + | | | |
| 2.0% NaCl | + | | | |
| 2%~10% acetate | − | | | |

[1] +: Positive,
[2] −: Negative,
[3] ND: Not Decided

As shown in Table 3, as a result of inoculating Frateur culture medium with the novel D44 strain, $CaCO_3$ inside the culture medium was neutralized, forming a clear zone. The $CaCO_3$ re-precipitated 12 days after culturing. Accordingly, the D44 strain oxidates ethanol to acetic acid, and acetic acid to $CO_2$ and $H_2O$. (Son. H. J., Kim. K. K., Kim. H. S., Kim. Y. G. 1999. Isolation and identification of cellulose-producing bacteria. J. Agri. Tech & Dev. Inst., Vol. 28, No. 3, 134-138).

Moreover, the D44 strain cannot form γ-pyrone using 5% (w/v) glucose and 5% (w/v) fructose and showed a positive response to the ketogenesis reaction from glycerol. The D44 strain is β-galactosidase positive, oxidates nitrate to nitrite, and oxidates acetate, glucose, fructose, and mannitol, but cannot oxidate lactate.

Furthermore, the D44 strain showed negative responses with respect to indole production, urease, and the gelatin liquefaction reaction. The D44 strain is able to grow and develop in 0.5, 1.0, 1.5, or 2.0% (w/v) sodium chloride, and can produce cellulose in 0.5% sodium chloride. It was observed, however, that the D44 strain showed no tolerance for and was not able to grow at 2% (v/v)-10% (v/v) acetate concentration. Instead of forming a brown pigment, D44 produced only a transparent, white colony.

Based on the results described above, the D44 strain disclosed herein is determined to be a *gluconacetobacter* strain.

TABLE 4

Biochemical features of D47 strain

| Features | D47 | *Acetobacter xylinum* KCCM40274 | *Gluconobacter oxidans* KCCM21183 | *Gluconacetobacter* |
|---|---|---|---|---|
| Overoxidation of ethanol | +[1] | + | −[2] | + |
| Ketogenesis from glycerol | − | + | + | + |
| Oxidation of acetate to $CO_2$ and $H_2O$ | + | + | − | + |
| Oxidation of lactate to $CO_2$ and $H_2O$ | − | + | − | + |
| Oxidation of Fructose to $CO_2$ and $H_2O$ | + | | ND | |
| Brown pigmentation on GYC agar | ± | + | − | − |
| Cellulose formation | + | + | − | + |
| Oxidase | − | − | − | − |
| Indole production | − | − | − | − |
| Urease | − | − | − | − |
| γ-pyrone from 5% glucose | − | − | + | − |
| γ-pyrone from 5% fructose | − | − | + | − |
| β-galactocidase | − | + | − | + |
| Nitrate to nitrite | − | + | + | − |
| Gelatin liquefaction | − | − | − | − |
| Acid produced from | | | | |
| Arabinose | − | − | − | + |
| Manose | − | ± | + | + |
| Manitol | + | + | + | + |
| Glucose | + | + | + | + |
| Growth in the presence of | | | | |
| 10% ethanol | − | − | − | − |
| 0.5% NaCl | + | | ND[3] | |
| 1.0% NaCl | + | | | |
| 1.5% NaCl | + | | | |
| 2.0% NaCl | + | | | |
| 2~10% acetate | − | | | |

[1] +: Positive,
[2] −: Negative,
[3] ND: Not Decided

As shown in Table 4, as a result of inoculating Frateur culture medium with the novel D47 strain, $CaCO_3$ inside the culture medium was neutralized, forming a clear zone. The CaCO₃ re-precipitated 8 days after culturing. Accordingly, the D47 strain oxidates ethanol to acetic acid, and acetic acid to $CO_2$ and $H_2O$. (Son. H. J., Kim. K. K., Kim. H. S., Kim. Y. G. 1999. Isolation and identification of cellulose-producing bacteria. J. Agri. Tech & Dev. Inst., Vol. 28, No. 3, 134-138.)

Moreover, the D47 strain cannot form γ-pyrone using 5% (w/v) glucose and 5% (w/v) fructose and unlike the D44 strain, showed a negative response to the ketogenesis reaction from glycerol. And the D47 strain is β-galactosidase negative, does not oxidate nitrate to nitrite. However, similar to the D44 strain, the D47 strain oxidates acetate, glucose, fructose, and mannitol, but cannot oxidate lactate.

Furthermore, the D47 strain showed negative responses with respect to indole production, urease, and the gelatin liquefaction reaction. The D44 strain is able to grow and develop in 0.5, 1.0, 1.5, or 2.0% (w/v) sodium chloride, and can produce cellulose in 0.5% sodium chloride. It was observed, however, that the D47 strain showed no tolerance for and was not able to grow at 2% (v/v)-10% (v/v) acetate concentration. Unlike the D44 strain, the D47 strain produced a pale brown colony.

Based on the results described above, the D47 strain disclosed herein is determined to be a *gluconacetobacter* strain.

EXAMPLE 2-3

16s rDNA Analysis

In order to extract ribosomal DNA (rDNA) from the isolated D44 and D47 strains in Example 1, 1% (v/v) cellulase (Celluclast, nonzyme) was added to a D44 culture to remove cellulose formed on the air-liquid interface of the H.S. culture medium, and the mixture was cultured with agitation for 1 hr at 37° C. 16s rDNA was extracted and amplified using a DNeasy Blood & Tissue kit (QIAGEN, Germany). A complete sequence of the 16s rDNA of the D44 strain (SEQ ID NO: 1) and a complete sequence of the 16s rDNA of the D47 strain (SEQ ID NO: 2) were obtained by sequencing.

For cloning of the 16s rDNA of the D44 and D47 strains, polymerase chain reaction (PCR) amplification was performed using SEQ ID NO: 3 (5'-AGAGTTTGATCMT GGCTCAG-3'(Forward)) and SEQ ID NO: 4 (5'-ACGGGCGGGTGTGTRC-3'(Reverse)) as the primer pair.

In particular, the PCR amplification was performed through 35 cycles consisting of denaturing for 30 sec at 95° C., annealing for 30 sec at 58° C., and extending for 90 sec at 72° C. with a Biometra thermocycler using 100 ng template DNA, 0.5 uM primer DNA, 0.2 mM dNTPs, 10× EX TAQ buffer solution, and 0.025 U/ul Taq polymerase (TaKaRa Bio Inc., Japan). The PCR product was detected by 1% agarose gel electrophoresis, and subsequently purified with a PCR purification kit (Bioneer, Korea) followed by cloning into a pGEM T-easy vector (Promega, U.S.A) by T4 ligase (Promega, USA). The nucleic acid sequence information of the 16s rDNA of the D44 and the D47 strains were obtained by sequencing.

For identification reference, the homology of the D44 and the D47 16s rDNA sequence to that of ribosomal DNAs recorded in GenBank was examined. Using the computer programs Bioedit (a biological sequence alignment editor written by Tom Hall and available free on the internet), Clustal X (Jeanmougin F, Thompson J D, Gouy M, Higgins D G, Gibson T J. (1998). Multiple sequence alignment with Clustal X. Trends Biochem Sci., 23, 403-405), and MEGA (Kumar S, Dudley J, Nei M & Tamura K (2008) MEGA: A biologist-centric software for evolutionary analysis of DNA and protein sequences. Briefings in Bioinformatics 9: 299-306.) a phylogenetic tree of similarly identified microorganisms was drawn to observe the relationship among similar species.

The comparison of the rDNA sequence of the D44 strain to 16s rDNA sequence (AY180961) of *Gluconacetobacter rhaeticus* showed that the percentage of homology was limited to 87.215%. Usually, 98-99% homology of two sequences is required to conclude that the bacteria belong to the same strain. Since the homology ratio between the D44 strain and *Gluconacetobacter rhaeticus*, however, was only 87.215%, the D44 strain disclosed herein is a novel *gluconacetobacter* strain.

Figure 2A:
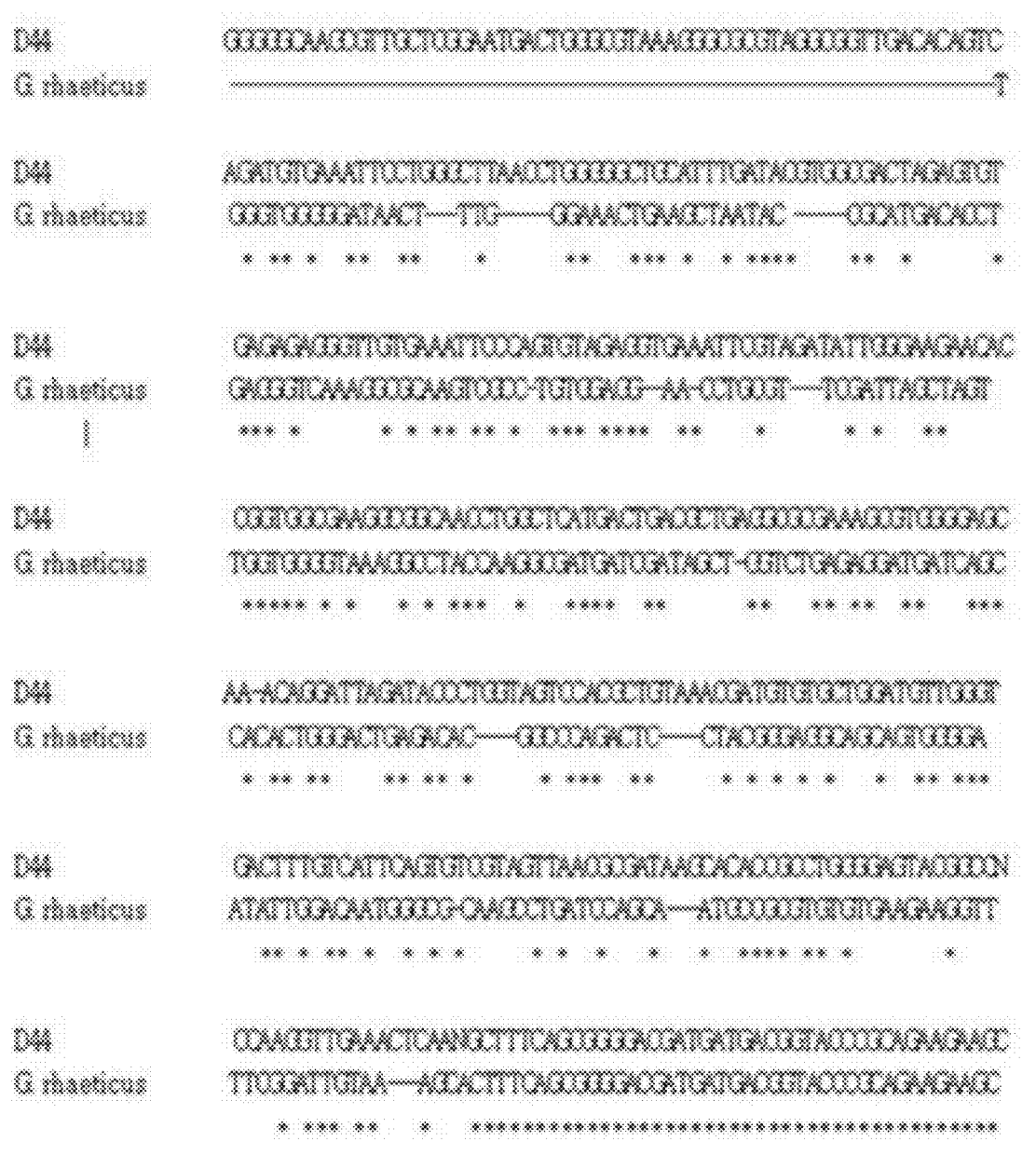
Figure 2B:
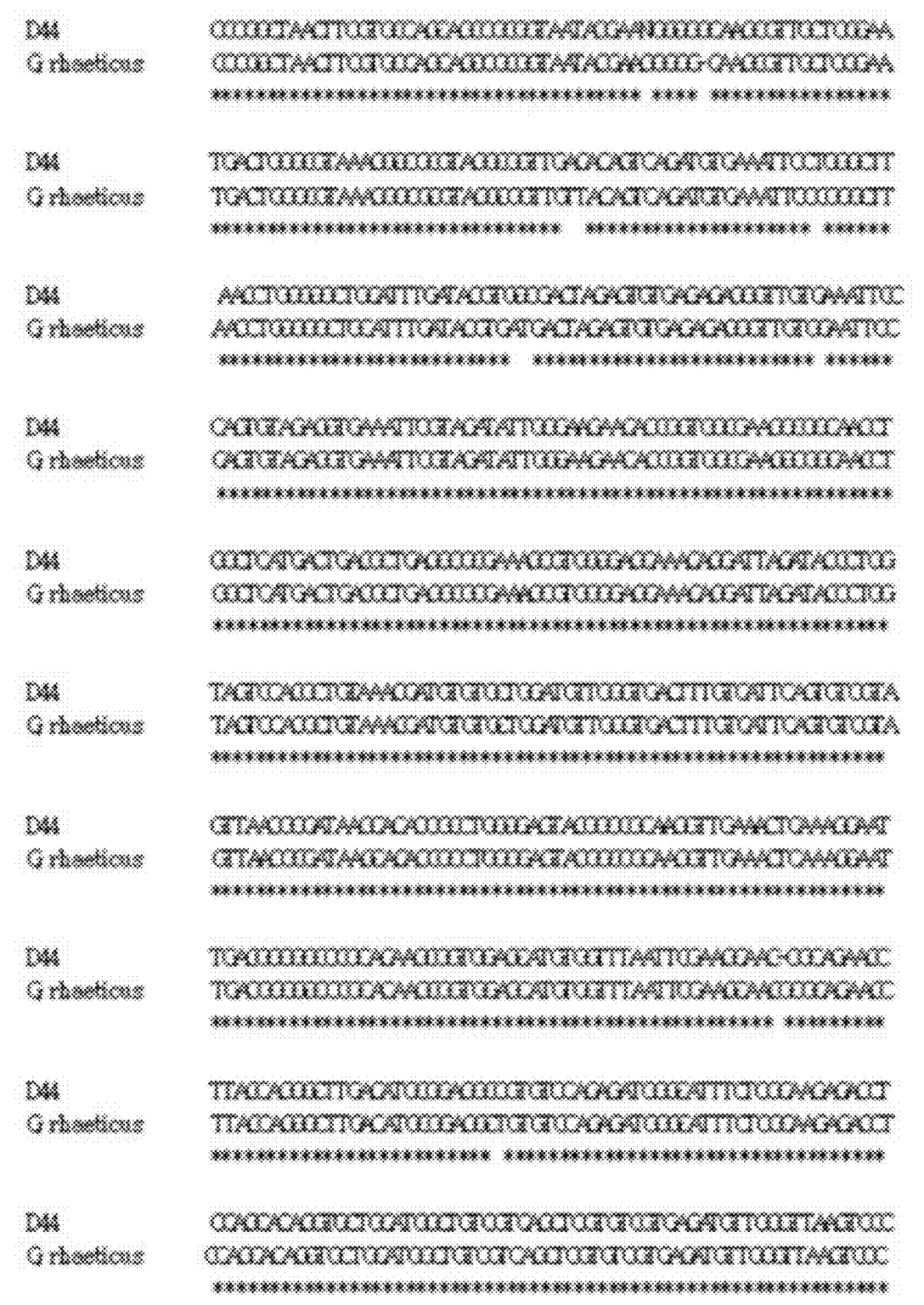
Figure 2C:
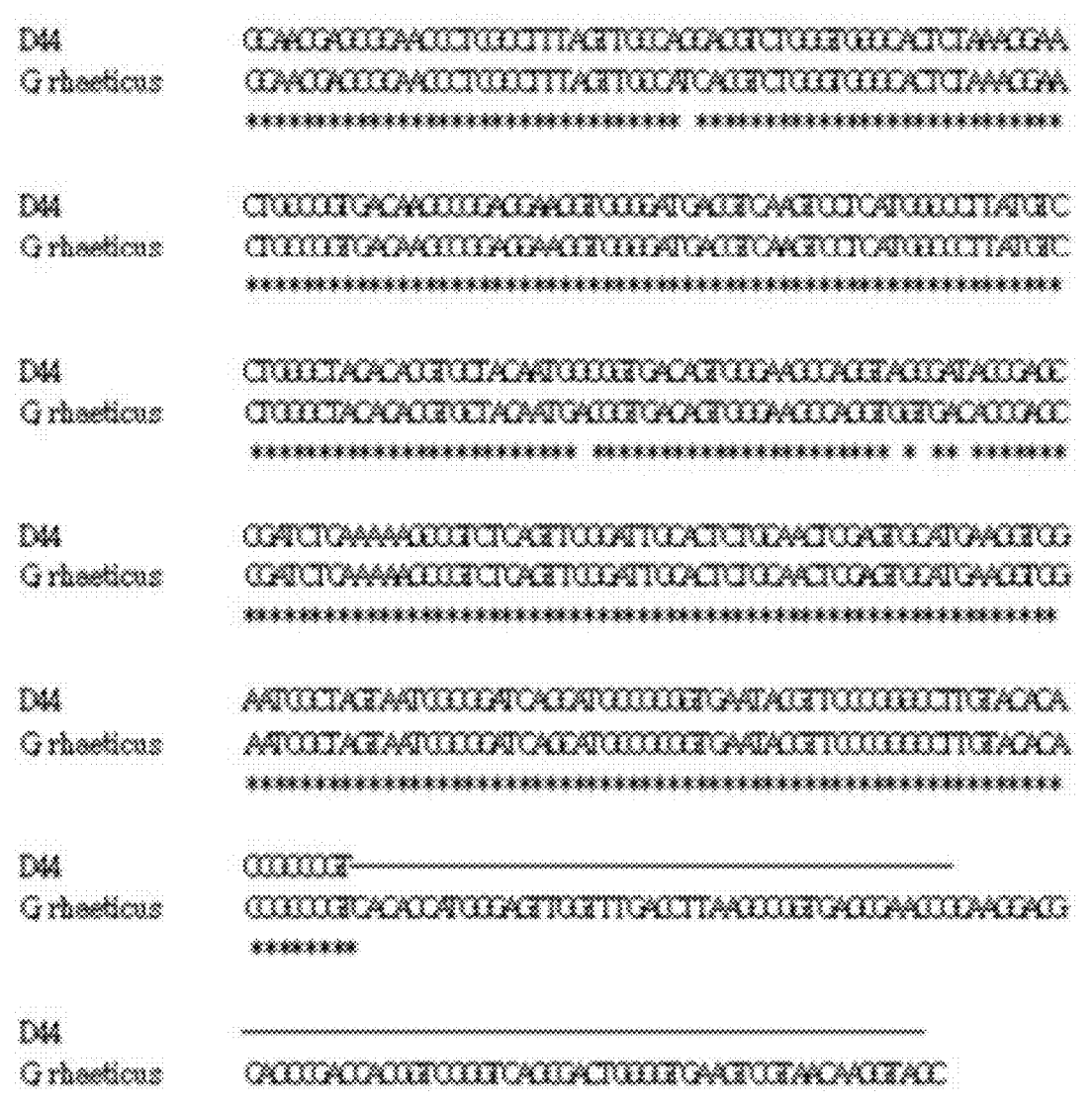

Moreover, as shown in FIG. 2A-2C, the homology of D44 and *Gluconacetobacter rhaeticus* was confirmed with Clustal X. The homology percentage of D44 and *Gluconacetobacter rhaeticus* was limited to 87.215%.

Figure 3:
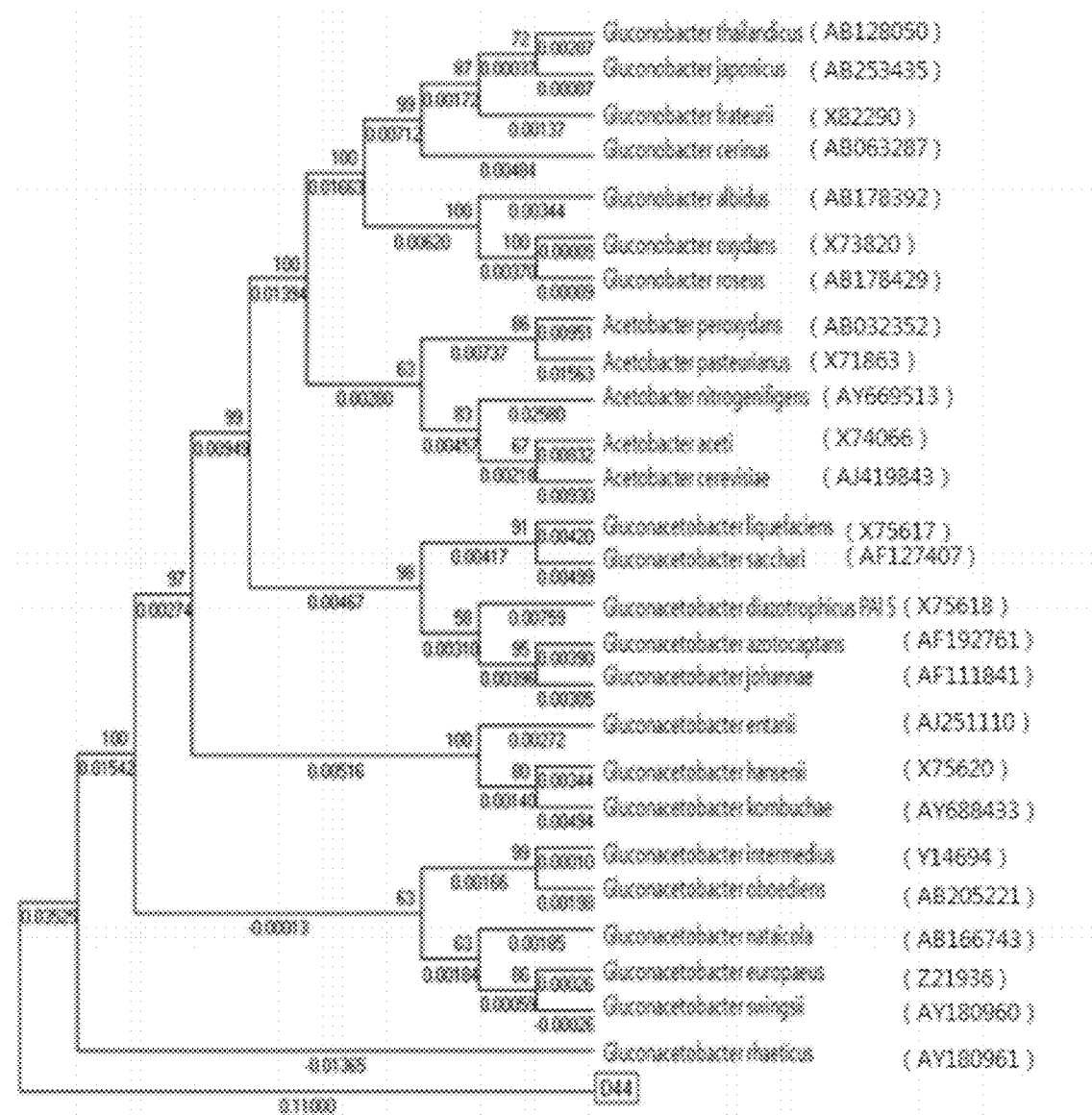
FIG. 3 is a phylogenetic tree of gluconacetobacter, gluconobacter, acetobacter bacteria of the acetobacter family, including the D44 strain of the present invention.

Bioedit, Clustal X, and MEGA were used to examine the phylogenetic relationship of D44 and microorganisms belonging to the identical family, acetobacteraceae. Specifically, as shown FIG. 3, a phylogenetic tree of *gluconacetobacter, gluconobacter, acetobacter* bacterial strains was prepared by applying a Neighbor-joining method.

The comparison of the rDNA sequence of the D47 strain to 16s rDNA sequence (Y14694) of *Gluconacetobacter intermedius* showed that the percentage of homology was 99.774%. Accordingly, the D47 strain is concluded to be analogous bacteria and was designated to be *gluconacetobacter intermedius* D47.

Figure 6A:
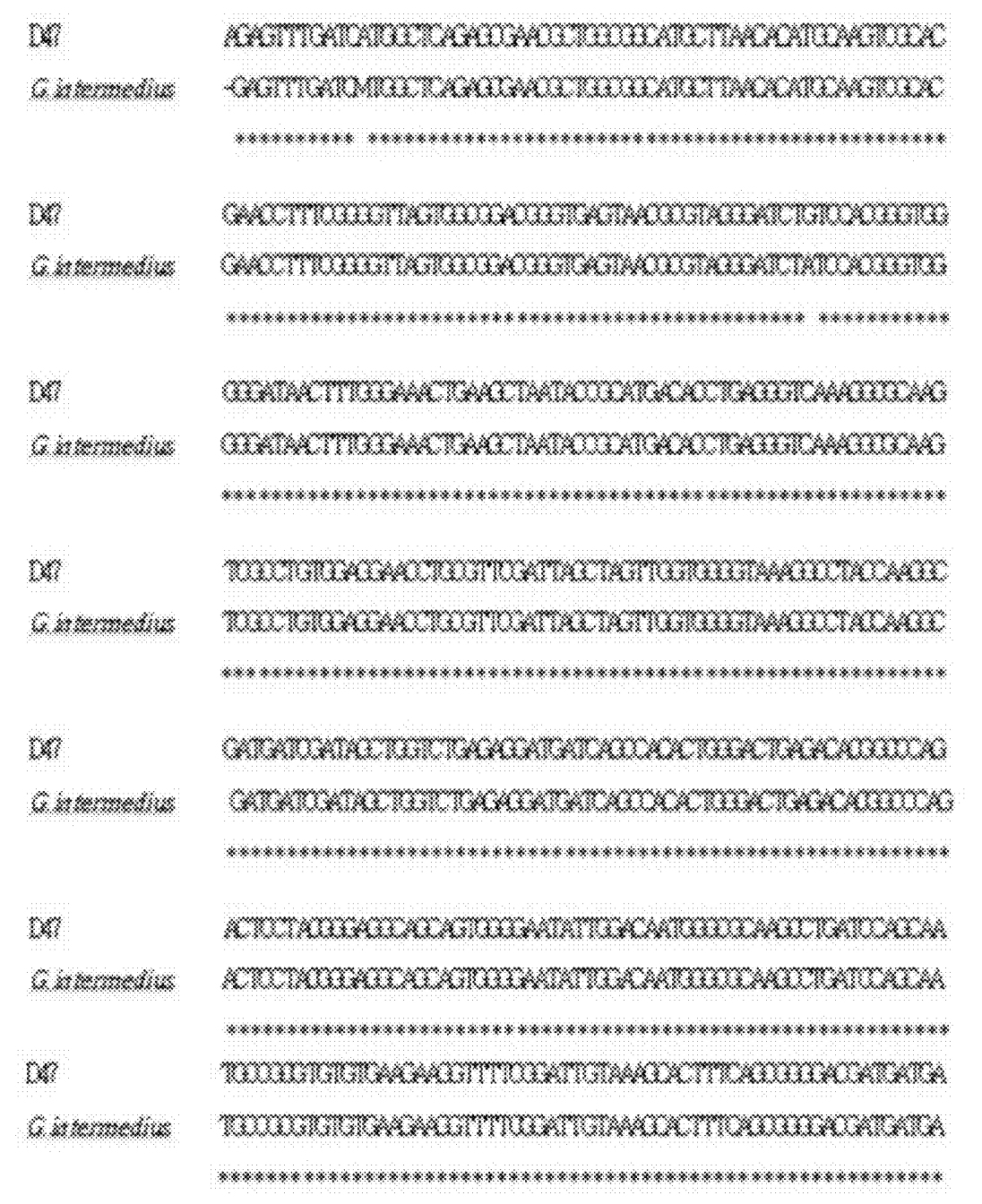
Figure 6C:
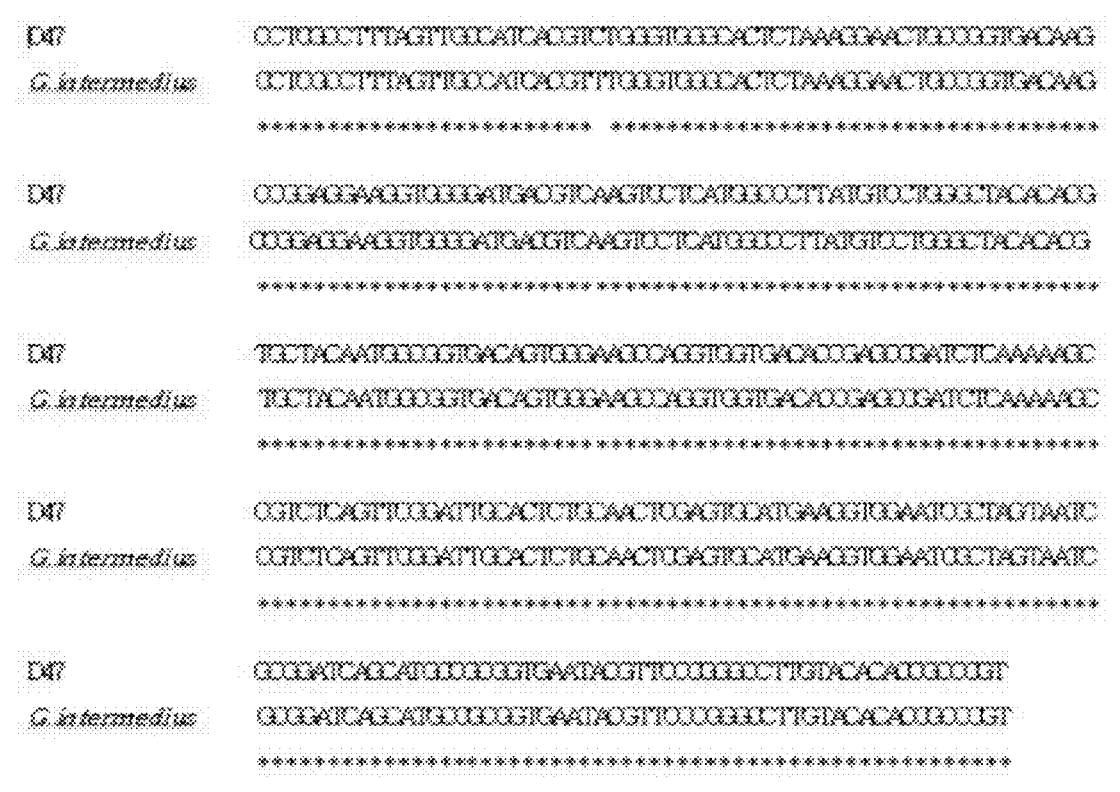

Moreover, as shown in FIG. 6A-6C, the homology of D47 and *Gluconacetobacter intermedius* was confirmed with Clustal X. The homology percentage of D47 and *Gluconacetobacter intermedius* was 99%.

As shown in Table 4 of Example 2-2, however, the D47 strain, unlike traditional *gluconacetobacter* strain, showed dihydroxyacetone forming ketogenesis reaction in glycerol, was not able to oxidate lactate, and produced cellulose on the medium surface during culturing in H.S. medium added with 0.5% (w/v) NaCl. These results confirm that D47 is a novel gluconacetobacter strain having biochemical features that are completely different from the traditional gluconacetobacter. In terms of cellulose producing ability, the D47 also showed prominently higher producing activity compared to traditional *gluconacetobacter* strain as discussed more in detail below.

Figure 7:
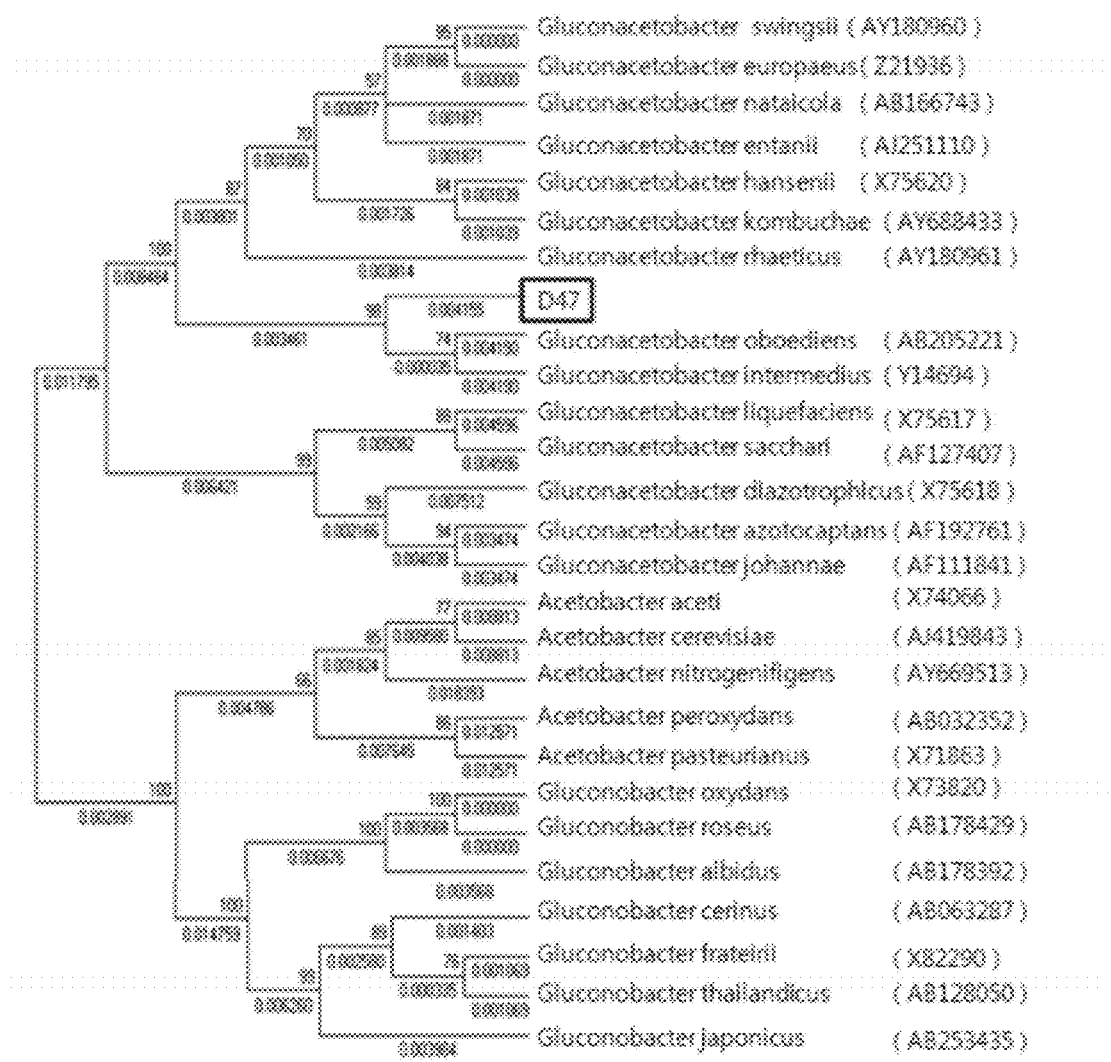
FIG. 7 is a phylogenetic tree of gluconacetobacter, gluconobacter, acetobacter bacteria of the acetobacter family, including the D47 strain of the present invention.

Bioedit, Clustal X, and MEGA were used to examine the phylogenetic relationship of D47 and microorganisms belonging to the identical family, acetobacteraceae. Specifically, as shown FIG. 7, a phylogenetic tree of *gluconacetobacter, gluconobacter, acetobacter* bacterial strains was prepared by applying a Neighbor-joining method.

EXAMPLE 2-4

Deposit of the D44 and the D47 Strains

Each of the novel, isolated and identified *Gluconacetobacter* strains disclosed herein were deposited at the Korean Culture Center of Microorganisms (KCCM) on Mar. 26, 2010 and received Accession No: KCCM11078P(D44) and Accession No: KCCM11079P(D47).

EXAMPLE 3

Cellulose Producing Activity of Strain of the Present Invention

EXAMPLE 3-1

Cellulose Producing Activity of Strain of the Present Invention

Figure 4:
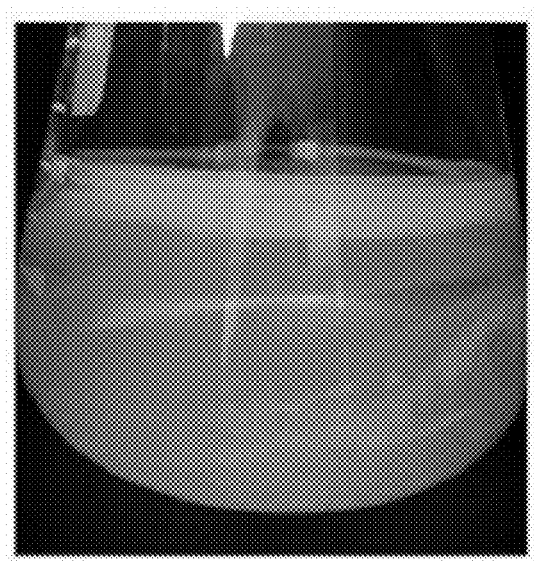
FIG. 4 presents image of a culture flask showing cellulose formed by the D44 stain during culture in H.S. culture medium.
Figure 8:
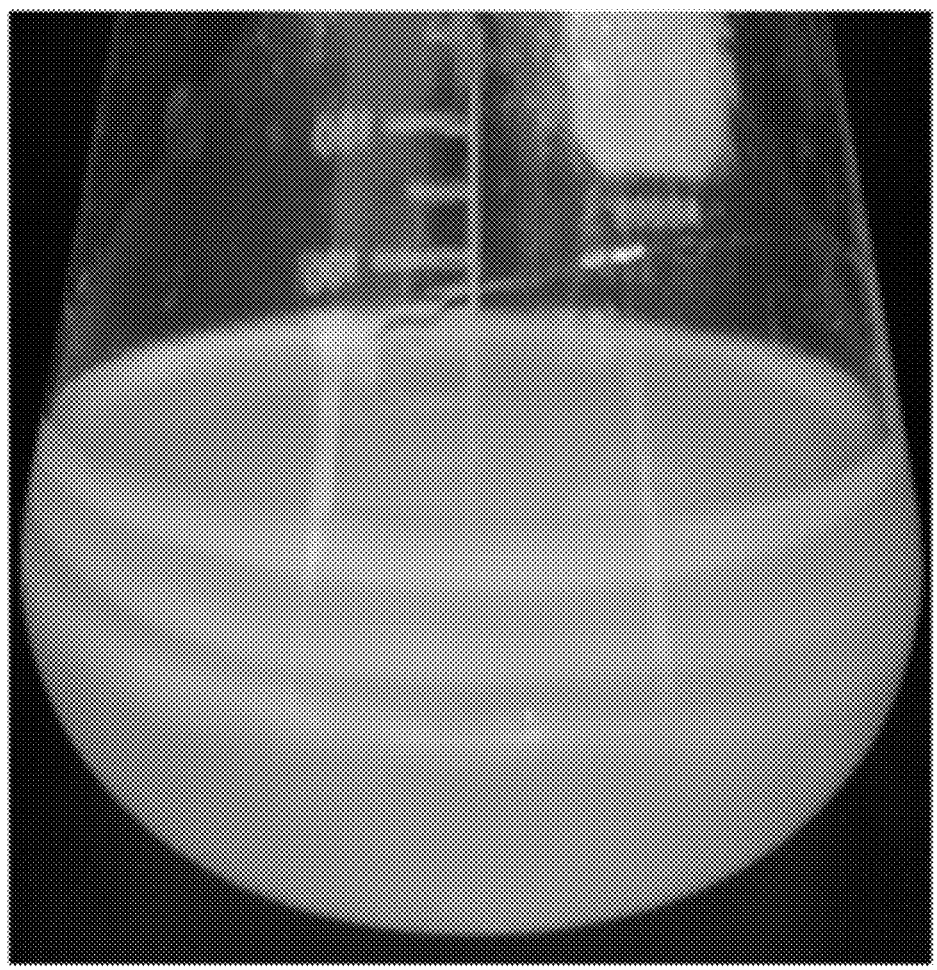
FIG. 8 presents image of a culture flask showing cellulose formed by the D47 stain during culture in H.S. culture medium.

Cellulose production by the D44 and the D47 strains were examined in H.S. culture medium and the result is shown in FIG. 4 and FIG. 8.

As shown in FIG. 4 and FIG. 8, after culturing for 2-3 days, the D44 and the D47 strains extruded cellulose at the air-liquid interface of the culture. As extruded cellulose accumulated as the culturing period extended, the culture thickened.

Figure 9A:
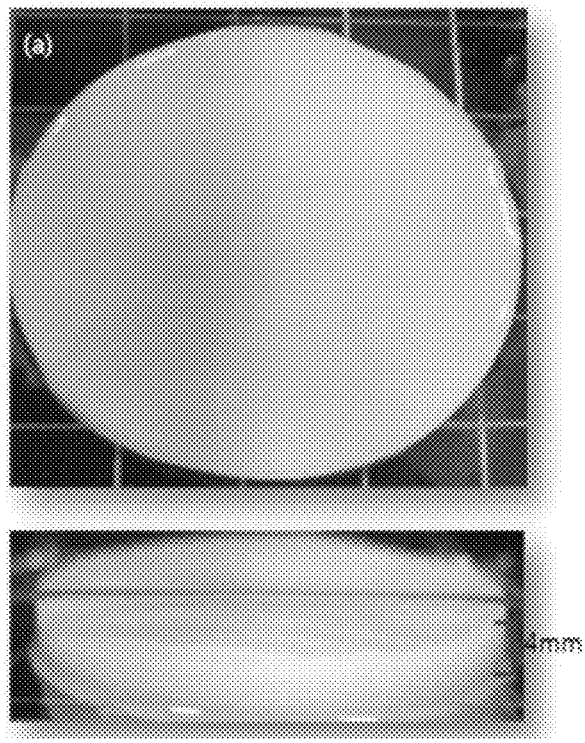
FIGS. 9A, and 9B present images of the cellulose produced by culturing D47 strain in H.S. medium (FIG. 9A) and coconut mixed medium (2) (FIG. 9B).

After inoculating H.S. culture medium with each of the D44 and the D47 strains at 1 weight % (based on the total weight of culture medium), and stationary culturing for 7 days at 30° C., the dry weight of the cellulose produced was measured (Table 5 and FIG. 9A). Specifically, upon completion of stationary culturing, the cellulose formed at the air-liquid interface of the H.S. culture medium was collected, washed with tap water, and then inserted into a small quantity of 0.1N NaOH which was boiled for 1 hr prior to cell lysis. The collected cellulose was re-washed with tap water and neutralized by inserting into a small quantity of distilled water for 1 day. The neutralized cellulose was filtered, dehydrated at 90° C. until it reached a constant weight, cooled in desiccators, and then the dry weight was measured.

TABLE 5

Dry weight of cellulose (BC) produced by D44 and D47 strains

|  | BC production(Dry weight, g/L) |
| --- | --- |
| D44 | 1.70 ± 0.91 |
| D47 | 2.17 ± 0.37 |

The cellulose produced by the D44 strain disclosed herein and treated as described above had a smooth, firm, and elastic surface and a thickness of approximately 0.3 mm. The cellulose produced by the D47 strain disclosed herein and treated as described above had a smooth, firm, and elastic surface and a thickness of approximately 4 mm. Furthermore, the D47 strain showed much higher cellulose producing activity. As discussed more in detail below, the thickness of cellulose produced by D47 strain in coconut mixed medium (2) was approximately 12 mm and showed prominently higher cellulose producing activity.

EXAMPLE 3-2

Comparison of Cellulose Producing Activity of Strain of the Present Invention The cellulose producing activity each of the D44 and D47 strains were compared to that of *Acetobacter xylinum*, a microorganism well known for cellulose production.

H.S. culture medium was inoculated with each of the D44 and D47 strain or *Acetobacter xylinum* KCCM 40274 at 1 weight % (based on the total weight of the culture medium), and subjected to stationary culture for 7 days at 30° C. The dry weight of cellulose produced by each was measured as described in Example <3-1>. The results are shown in Table 6.

TABLE 6

Dry weight of cellulose (BC) produced by D44 and D47 strains or *Acetobacter xylinum* KCCM 40274

|  | *Acetobacter xylinum* KCCM 40274 | *Gluconacetobacter* sp. D44 | *Gluconacetobacter intermedius* D47 |
| --- | --- | --- | --- |
| BC yield (g/L) | 0.50 ± 0.28 | 1.70 ± 0.91 | 2.17 ± 0.37 |

As shown in Table 6, the D44 strain disclosed herein can produce approximately three times as much cellulose as the *Acetobacter xylinum*, and the D47 strain disclosed herein can produce approximately 4.34 times as much cellulose as the *Acetobacter xylinum*. It is noteworthy that the D47 strain showed approximately 1.27 times as much cellulose producing activity as the D44 strain.

REFERENCE EXAMPLE 2

Mediums Used for Evaluation of Cellulose Production and Culturing Conditions Based on Medium Composition In order to determine the effect of medium composition, one of the factors that promotes cellulose production by the strains disclosed herein in H.S. medium, bacteria was cultured in the medium prepared by composition described in Table 7.

Bacteria culturing solution was adjusted to be 1% (v/v) and the temperature was maintained to be 30° C. Upon 7 days culturing, the dry weight was measured and average value obtained through repeated experiments was used.

TABLE 7

Medium composition for culturing D44 and D47 strains

| Medium composition | H.S medium | Coconut liquid medium | Coconut mixed medium(1) | Coconut mixed medium(2) |
| --- | --- | --- | --- | --- |
| Glucose | 20 g/L | — | — | — |
| Yeast Extract (difco, USA) | 5 g/L | — | — | — |
| Peptone | 5 g/L | — | — | — |
| $Na_2HPO_4$ | 2.7 g/L | — | — | — |
| Sodium citrate | 1.15 g/L | — | — | — |
| Undiluted coconut solution[1] | — | 1000 g/L | 895 g/L | 895 g/L |
| Sugar | — | — | 100 g/L | 100 g/L |
| Ammonium Sulfate[2] | — | — | 5 g/L | — |
| Ammonium Sulfate[3] | — | — | — | 5 g/L |
| pH, temperature (° C.) | 5, 30 | 5, 30 | 5, 30 | 5, 30 |

[1]Undiluteed coconut solution: 100% undiluted solution imported from www.onedrinks.com (One world enterproses, LLC, USA. mede in brazil)
[2]Ammonium Sulfate: purity of 99% ammonium sulfide manufactured by Sigma(USA)
[3]Ammonium Sulfate: purity of 21% ammonium sulfide manufactured by Chia Tai Co., Ltd. (Thailand)

EXAMPLE 4

Experiment for Promoting Cellulose Producing Activity by the Strains of the Present Invention Depending on Medium Composition As shown in Table 7, the medium composition varied to measure the dry weight and thickness of the cellulose produced by the D44 and the D47 strains disclosed herein and the results were listed in Table 8. The results were compared to *Actobacter xylinum* strain (KCCM40274) used in Example 3-2.

TABLE 8

Comparison of dry weight of cellulose production based on medium composition

| Strain | Medium | Dry Weight (g/L) |
|---|---|---|
| *Acetobacter xylinum* (KCCM 40274) | H.S Medium | 0.10 |
| | Coconut Liquid Medium | 0.02 |
| | Coconut Mixed Medium(1) | 0.20 |
| | Coconut Mixed Medium(2) | 0.20 |
| *Gluconactetobacter* sp. D44 | H.S Medium | 1.90 |
| | Coconut Liquid Medium | 1.00 |
| | Coconut Mixed Medium(1) | 0.20 |
| | Coconut Mixed Medium(2) | 0.20 |
| *Gluconacetobacter intermedius* D47 | H.S Medium | 2.20 |
| | Coconut Liquid Medium | 1.95 |
| | Coconut Mixed Medium(1) | 0.80 |
| | Coconut Mixed Medium(2) | 5.10 |

As shown in Table 8, the D44 and the D47 strains disclosed herein generally showed much higher cellulose production yield compared to *acetobacter xylinum*, a representative strain for producing cellulose. Especially, the D47 strain produced the greatest amount of cellulose in all mediums.

Specifically, the dry weight of cellulose produced by the D44 strain was 19 times as much in H.S. medium and 50 times as much in coconut liquid medium as the *acetobacter xylinum* strain. The dry weight of cellulose produced by D47 strain was 22 times as much in H.S. medium and 97.5 times as much in coconut liquid medium as the *acetobacter xylium* strain. These results confirm that the strain of the present invention produced cellulose with much higher yield.

Meanwhile, the comparison of cellulose production yield between *acetobacter xylium* strain and the D44 showed no significant difference in coconut mixed medium (1), (2). However, the D47 strain disclosed herein showed the dry weight of produced cellulose was 0.80 g/L in coconut mixed medium (1), and 5.10 g/L in coconut mixed medium (2). When compared to *acetobacter xylium* strain, each of these figures are 4 times and 25.5 times higher in coconut mixed medium (1), (2), respectively. The result further confirms that the D47 strain produces cellulose with higher yield than the D44 strain.

In conclusion, the strains disclosed herein can produce cellulose with much higher yields relative to *acetobacter xylium*, a representative strain for producing cellulose, and such cellulose producing efficiency can be varied depending on medium composition.

Figure 9B:
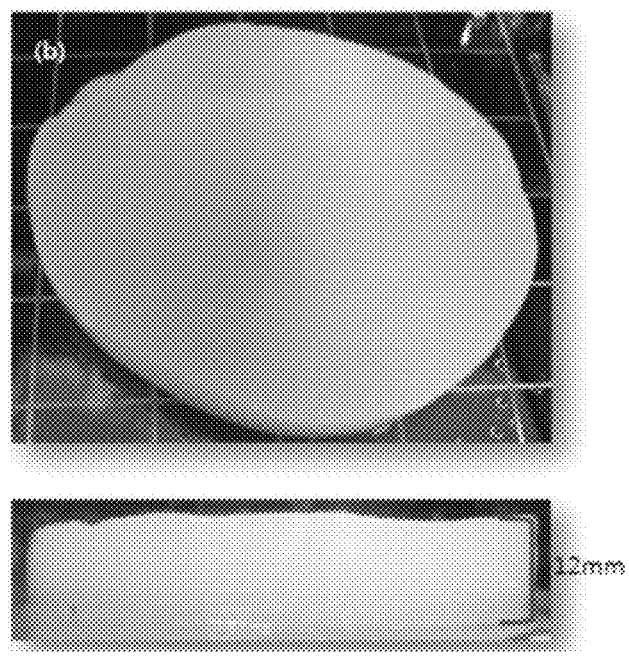

In other words, whereas the D44 strain produced 9.5 times as much cellulose in H.S. medium as the cellulose in coconut mixed medium, D47 strain produced 2.32 times as much cellulose in coconut mixed medium (2) prepared by adding sugar and ammonium sulphate into undiluted coconut solution, and 6.4 times as much cellulose in coconut mixed medium (1) as the cellulose in H.S. medium. Moreover, the measurement of thickness of cellulose produced by D47 strain in coconut mixed medium (2) showed that significantly increased thickness of 12 mm, which was 3 times thicker than 4 mm measured in H.S. medium, could be observed (FIGS. 9A and 9B).

What is claimed is:

1. An isolated *gluconacetobacter* strain designated with Accession No: KCCM11078P, and having cellulose producing activity.

2. The *gluconacetobacter* strain according to claim 1, wherein the strain having Accession No: KCCM11078P has the 16s rDNA nucleotide sequence of SEQ ID No: 1.

3. A culture of the *gluconacetobacter* strain according to claim 1.

4. The culture according to claim 3 wherein said culture comprises cellulose.

5. A composition for cellulose production comprising
   at least one selected from the group consisting of the *gluconacetobacter* strain according to claim 1,
   a culture thereof,
   a concentrate of the strain or the culture, and
   a dried product of the strain or the culture.

6. A method for producing cellulose comprising the steps of:
   culturing the *gluconacetobacter* strain according to claim 1; and
   obtaining cellulose from the culture.

7. The method according to claim 6, wherein the culturing step of *glucoacetorbacter* strain having Accession No: KCCM11078P is performed in H.S. medium comprising glucose 20 g/L, yeast extract 5 g/L, peptone 5 g/L, Na2HPO4 2.7 g/L and sodium citrate 1.15 g/L.

8. A method for producing a cellulose-based resin comprising the steps of:
   preparing the cellulose produced by the *gluconacetobacter* strain according to claim 1; and
   impregnating the cellulose with a resin.

9. The method according to claim 8, wherein the cellulose-based resin is adapted for a substrate of liquid crystal display (LCD).

\* \* \* \* \*